United States Patent [19]

Baxter et al.

[11] 4,056,716

[45] Nov. 1, 1977

[54] DEFECT INSPECTION OF OBJECTS SUCH AS ELECTRONIC CIRCUITS

[75] Inventors: Duane Willard Baxter, Rochester, Minn.; Richard Edward Shipway, Endwell, N.Y.

[73] Assignee: International Business Machines Corporation, Armonk, N.Y.

[21] Appl. No.: 701,337

[22] Filed: June 30, 1976

[51] Int. Cl.² .............................................. H04N 1/38
[52] U.S. Cl. ....................................... 364/515; 178/6; 324/73 PC; 358/106
[58] Field of Search .................... 235/151.31, 151.3; 178/DIG. 37, 6; 324/73 PC; 73/355

[56] References Cited

U.S. PATENT DOCUMENTS

| 3,463,007 | 8/1969 | Jones et al. | 73/355 |
| 3,613,081 | 10/1971 | Morimoto | 340/146.3 H |
| 3,760,355 | 9/1973 | Bruckert | 340/146.2 |
| 3,790,767 | 2/1974 | Alexander | 235/151.31 |
| 3,812,426 | 5/1974 | Illian | 324/73 R |
| 3,816,719 | 6/1974 | Trotel et al. | 235/151 |
| 3,887,762 | 6/1975 | Uno et al. | 178/DIG. 37 X |
| 3,889,053 | 6/1975 | Lloyd et al. | 178/DIG. 37 X |
| 3,908,118 | 9/1975 | Micka | 235/181 |
| 3,991,302 | 11/1976 | Danner | 235/151.31 |

Primary Examiner—Edward J. Wise

[57] ABSTRACT

Successive areas of a high-resolution object image are compared with corresponding areas of a low-resolution master pattern to produce signals representing the quality of the object. Comparison is effected by detecting which of a set of features occurs in each area of the object image, detecting which feature of the same set occurs in a larger area of the master pattern, and determining whether these two features are the same.

8 Claims, 2 Drawing Figures

DEFECT INSPECTION OF OBJECTS SUCH AS ELECTRONIC CIRCUITS

BACKGROUND

The present invention pertains to the automatic inspection of manufactured articles or objects.

The constantly decreasing size and increasing complexity of electronic circuits challenge the state of the art in a number of technical fields. One of these fields involves the inspection of manufactured circuits for defects such as open-circuited conductors or adjacent conductors shorted to each other. An exemplary manufactured circuit may comprise a ceramic substrate about 2.5cm wide by 12.5cm long, containing plated silver or copper conductors spaced about 0.3mm apart. The conductors may have corners and junctions. They may terminate at pads for mounting individual semiconductor chips or for external package pins; they may also terminate at via holes which join conductors on the other side, for instance. When circuit substrates of this type are designed, the conductors, pads, etc. are laid out in a grid of small cells or areas which may be, e.g., squares 0.15mm on a side.

Inspection of such an object requires a high-resolution image, to detect hairline conductor cracks, dendritic bridges between conductors, and other small defects. But the direct comparison with a master or ideal pattern at this high resolution has two disadvantages. First, a high-resolution master pattern would require almost a million bytes of storage for the above exemplary substrate, even if each pattern cell required only a single bit. Second, it is highly unlikely that a direct comparison would produce an exact match, even if the object contains no defects at all. Rough edges on conductors, stray isolated bits of foreign material, noise from the scanning process, etc. would all produce a significant number of apparent errors. Therefore, it is not feasible to inspect such an object by direct comparison with a master pattern.

SUMMARY

The primary purpose of the present invention is to provide a method and apparatus for inspecting manufactured objects or articles for defects. Since a straightforward comparison with an ideal or master pattern is impractical, the present invention instead proposes to store a low-resolution image of the master pattern. That is, each cell or area of the master pattern covers a large area than each cell or area of a high-resolution electronic representation or image obtained by scanning the object. A set of "features" is defined for a window or group of cells in the high-resolution image. The features detected in the window are compared with features detected in a window of the low-resolution master pattern. The latter window corresponds to a larger area of the object than the high-resolution window, but it includes that area. Then, instead of comparing the object and the pattern with each other directly, the two features are compared: if they are the same, the object is satisfactory. This process is repeated so as to cover the entire object with the window.

DRAWINGS

DETAILED DESCRIPTION

Figure 1:
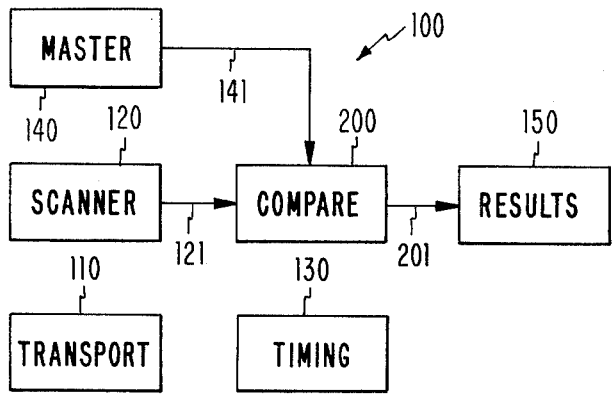
FIG. 1 is a block diagram of an inspection system 100 in which the present invention finds utility.

FIG. 1 is a block diagram of a machine 100 for inspecting articles such as the ceramic green sheets mentioned hereinabove. A mechanical transport 110 moves a green sheet (not shown) past a scanner 120, which can be of any conventional type. For illustrative purposes, it will be assumed that transport 110 carries green sheets longitudinally at a constant velocity past a transverse, flying-spot scan line from scanner 120. Scanner 120 divides the image into individual small areas or cells according to signals from timing means 130, as in conventional practice. Each of the cells is digitized to one of two levels, "white" (representing the background or substrate) and "black" (representing the pattern). The video signal on line 121 is a high-resolution electronic representation or image, each sample of which represents the digitized value of a small square cell of the object to be inspected. Such a cell may be, for example, 0.025mm on a side.

Storage unit 140 holds a master pattern; i.e., an image of an ideal specimen of the type being scanned by unit 120. This master pattern, which appears serially on line 141, is also divided into small areas or cells. These cells, however, are much larger; they may be, e.g., about 0.15mm on a side. That is, line 141 carries a low-resolution image. Comparison unit 200 compares the image of an actual object (line 121) with the image of an ideal specimen (line 141), to produce correspondence signals on line 201. These signals indicate that corresponding cells of the images 121 and 141 are sufficiently similar to each other. (Such signals may also, of course, be taken to indicate exception conditions, where the two images differ significantly.) Result unit 150 stores the correspondence signals 201 for use in evaluating the scanned object as a whole; e.g., to determine whether the defects are serious enough to cause a rejection of the object. Result unit 150 and/or storage unit 140 may be implemented in a general-purpose digital computer, which may also perform other functions not directly related to the present invention. All units of FIG. 1, except for comparison unit 200, may be of conventional design.

Figure 2:
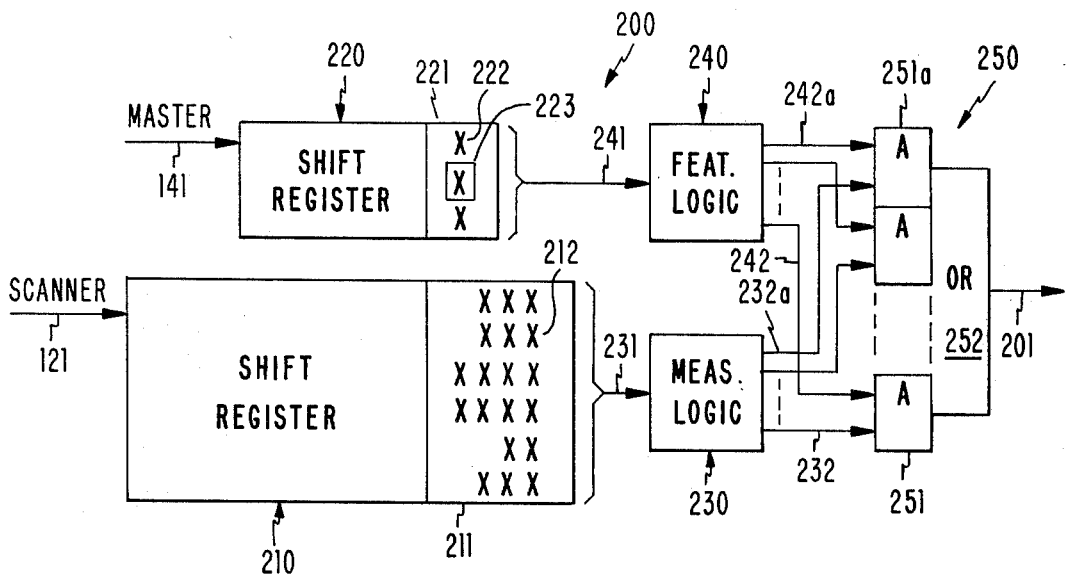
FIG. 2 is a block diagram of comparison unit 200 of FIG. 1, showing a preferred embodiment of the invention.

FIG. 2 shows comparison unit 200 in greater detail.

Digitized scanner data 121 moves through shift-register storage unit 210 from the upper left corner and emerges at the lower right, so as to form a conventional two-dimensional image of the object being scanned. Each row of register 210 has enough stages to hold one complete horizontal scan through the object to be inspected. For a 0.025mm cell size, each row may typically have about 4200 stages. Register 210 may typically have six such rows. Data are shifted through register 210 at equally spaced times $t_0, t_1, t_2, t_3, \ldots$, where $t_{i+1} = t_i + \Delta t$. (If scanner 120, FIG. 1, requires a retrace time longer than $\Delta t$, then every 4200th shift pulse may be delayed.) The rightmost six stages of each row form a window 211, representing an area of the scanned object six cells wide and six cells high. This corresponds to a 0.150mm square on the object. Pattern 212 represents an exemplary portion of the object as it may appear in window 211; the "X" marks represent conductive lands in a green sheet, while the blank spaces represent the insulating ceramic background.

Meanwhile, master-pattern data 141 moves through shift-register storage unit 220 from upper left to lower right. Each row of register 220 also holds a complete scan. But, since the cells in the master pattern may typically be 0.15mm square (i.e., six times the size of the pattern cells in register 210), only about 700 cells are required for each row. Window 221 comprises the last three stages of each of the three rows of register 220. Pattern 222 represents an exemplary portion of the master pattern as it may appear in window 221. Cell 223 represents a 0.15mm square of the low-resolution master pattern which corresponds to the 36 cells of the 0.15mm square on the high-resolution object patten in window 211. But window 221 also contains the eight other low-resolution cells surrounding cell 223. To mainatin this relationship over an entire scan field, master-pattern data begins six scan lines before data 121 representing the first scan across the object enters register 210. That is, data 121 is always six complete scans behind data 141. Register 220 also shifts at only one-sixth the rate of register 210, and does not shift at all during five scans out of every six. In this way, registers 210 and 220 always remain synchronized with each other, so that cell 223 always represents an area of the master pattern corresponding to the object area contained in window 211.

Assume that the object being scanned in an insulating substrate having an array of conductors deposited thereon at spacings which are integral multiples of 0.3mm, twice the cell size of the master pattern from unit 140, FIG. 1. The purpose of system 100 is to determine whether any of these conductors are either shorted together or open-circuited during manufacture. The manner in which system 100 achieves this function is to determine, for every 0.15mm square of the object being inspected, whether a certain desired "feature" is present or not. If that feature is detected, a match is recorded; if not, an error is signalled. Such features may include vertical, horizontal and diagonal lines, perpendicular or oblique (135°) corners, junctions of two or more lines and "via holes", either isolated or at the ends of lines. (A via hole is a conductive path between two levels, perpendicular to the surface of a substrate.) The example shown in FIG. 2 represents a vetical line.

The particular feature present in the current 0.15mm cell is detected by Boolean measurement logic 230. This logic receives inputs 231 from the shift-register stages in window 211. It preferably comprises multi-level AND-OR gates, of the type conventionally used in character and pattern recognition machines. For the specific example of the pattern 212 shown in FIG. 2, a logic for detecting a vertical line might be represented as:

$$\overline{A1} \cdot \overline{B1} \cdot \overline{C1} \cdot \overline{D1} \cdot \overline{E1} \cdot \overline{F1} \cdot A3 \cdot B3 \cdot D3 \cdot E3 \cdot F3 \cdot A4 \cdot B4 \cdot C4 \cdot D4 \cdot E4 \cdot F4 \cdot \overline{A6} \cdot \overline{B6} \cdot \overline{C6} \cdot \overline{D6} \cdot \overline{E6} \cdot \overline{F6} \cdot (A2+A5) \cdot (B2+B5) \cdot (C2+C5) \cdot (D2+D5) \cdot (E2+E5) \cdot (F2+F5).$$

where the six rows of window 211 are indicated, from top to bottom, by the letters A-F, and the columns, from left to right by numbers 1-6. Each logic in unit 230 produces an output on one of the lines 232. The presence of a vertical line, for example, may produce a signal on line 232a.

In the low-resolution master pattern, a single cell, 223, represents the entire 0.15mm area which covers 36 separate cells in window 211. Since cell 223 in a single shift-register stage, the only information it contains is a one-bit indication of whether that area, as a whole, belongs to the pattern or to the background. Unlike window 211, it is not possible to extract a feature from cell 223. But window 221 also includes the eight 0.15mm cells surrounding cell 223. From this larger area (0.45mm square), it is possible to extract features of the same types as those detected by logic 230. Boolean feature logics 240 perform this function. Logics 240 are of the same general construction as logics 230. Logics 240 may be much simpler, however, since the master pattern is ideal; i.e., it contains no "noise" or other defects. The logic for the vertical-line pattern 222, for example, may be simply written as $$X2 \cdot Y2 \cdot Z2 \cdot \overline{X1} \cdot \overline{Y1} \cdot \overline{Z1} \cdot \overline{X3} \cdot \overline{Y3} \cdot \overline{Z3}$$

where X-Z represent the rows of window 221, while the columns are numbered 1-3. Logics for other features are equally obvious. Each logic produces a signal on one of the lines 242. The satisfaction of the vertical-line logic, e.g., generates a "1" signal on line 242a.

Feature comparator 250 combines signals 232 with signals 242 to produce output signal 201. To this end, AND gates 251 each receive a pair of inputs, one signal of the pair coming from measurement logic 230, the other from feature loics 240. The signals of each pair represent the detection of the same feature by their respective logics. That is, AND 251a receives lines 232a and 242a, both representing a vertical line; and so forth. The output of each AND gate is coupled to OR 252, whose output is the signal 201. Signal 201, which may be strobed out to unit 150, FIG. 1, by timing means 130 once every time register 220 shifts, is a "match" signal: it is high if and only if both of the logics 230 and 240 detect the same feature for the current 0.15mm square area on the object being inspected. Signal 201 could just as easily be inverted to form an "error" signal for each area or cell.

In FIG. 2, gating logic 250 is shown as being separate from the logic of detectors 230 and 240, the same physical gates may serve both conceptual functions. The outputs 242 of detector 240 may be input to detector 230 along with window-cell signals 231, and outputs 232 may then be transmitted directly to OR 252. Then the 30-way AND in the vertical-line equation hereinabove, e.g., would become a 31-way AND, the 31st term being output 242a.

Further modifications of this embodiment, as well as other features and advantages of the invention, will become apparent from the above description. In particular, additional circuitry (not shown) may be added, if desired, to register the image 212 more accurately with respect to master pattern 222, by conventional means such as fiducial marks on the object itself, or by other means not forming a part of the present invention. Also, the data required for storage of the master pattern could be further reduced by storing it in a run-length or other coded form, and decoding it in unit 140 before transmission over line 141. Units 230 and 240, although termed "logics", could be implemented in other known forms, such as resistor correlation matrices. Yet again, units 210 and 220 could be constructed from random-access storage with suitable addressing logic, instead of from shift registers.

Having described a preferred embodiment thereof, I claim as my invention:

1. A method of inspecting an object for defects, comprising the steps of:
   a. producing a high-resolution electronic representation of an object, said representation having a plurality of cells each corresponding to a first amount of area on said object;

b. storing a low-resolution master pattern having a plurality of cells each representing a second, substantially larger amount of area on said object;

c. detecting a first of a predetermined set of features in a first window comprising a plurality of said cells of said high-resolution representation;

d. detecting a second feature of said set in a second window comprising a plurality of said cells of said low-resolution master pattern, said second window representing a substantially larger total area on said object than the area represented by said first window;

e. comparing said first feature with said second feature; and f. repeating steps (c), (d) and (e) for different ones of said windows, representing further areas on said object.

2. Comparison means for an automatic inspection device, comprising:

a high-resolution register for receiving and shifting an image of an object to be inspected, said first register having a plurality of cells each representing different first areas on said object;

a low-resolution register for receiving and shifting a master pattern of an ideal form of said object, said low-resolution register being divided into a plurality of cells each representing different second areas on said object, each of said second areas corresponding to a plurality of said first areas on said object;

a first feature detector coupled to a group of said cells of said high-resolution register for detecting the presence of absence of a predetermined set of features;

a second feature detector coupled to a group of said cells of said low-resolution register for detecting the presence or absence of said set of features;

gating means coupled to said feature detectors for producing a signal indicating whether or not the particular features found by said first and second detectors are the same.

3. The comparision means of claim 2, wherein said group of cells of said high-resolution register includes a substantially smaller area on said object than a larger area included in said group of cells of said low-resolution register.

4. The comparison means of claim 3, wherein said larger area includes and surrounds said first area.

5. The comparison means of claim 3, wherein said smaller area has substantially the same extent as the area on said object corresponding to a single one of said cells of said low-resolution register.

6. The comparison means of claim 2, wherein both said high-resolution register and said low-resolution register comprise a shift register having a plurality of stages.

7. The comparison means of claim 2, wherein said first and said second feature detectors comprise Boolean logic gates having inputs coupled to said registers.

8. The comparison means of claim 7, wherein said gating means comprises Boolean logic gates having inputs coupled to said feature detectors.

* * * * *